United States Patent [19]

Powers et al.

[11] 4,081,462

[45] Mar. 28, 1978

[54] $C_{22}$-CYCLOALIPHATIC TRICARBOXYLIC FATTY ACID SOAPS

[75] Inventors: John R. Powers, Mount Pleasant; Frances C. Miller, Charleston, both of S.C.

[73] Assignee: Westvaco Corporation, New York, N.Y.

[21] Appl. No.: 760,566

[22] Filed: Jan. 19, 1977

Related U.S. Application Data

[63] Continuation-in-part of Ser. No. 622,254, Oct. 14, 1975, abandoned.

[51] Int. Cl.[2] ........................ C07C 61/38; C11D 9/00; C07C 87/10; C07C 91/06

[52] U.S. Cl. ................................ 260/501.1; 252/108; 252/117; 252/156; 260/501.17; 260/514 K

[58] Field of Search ............ 260/514 K, 501.17, 501.1

[56] References Cited

U.S. PATENT DOCUMENTS

| | | | |
|---|---|---|---|
| 3,734,859 | 5/1973 | Word | 252/108 |
| 3,753,968 | 8/1973 | Word | 260/97.6 |

*Primary Examiner*—Robert Gerstl

*Attorney, Agent, or Firm*—Ernest B. Lipscomb, III; Terry B. McDaniel

[57] ABSTRACT

Disclosed herein is full soaps and mono-soaps of a $C_{22}$-cycloaliphatic tricarboxylic acid of the formula

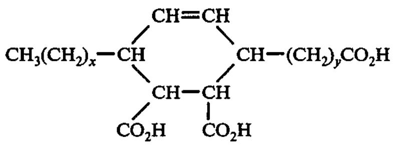

wherein x and y are integers from 3 to 9, and x and y together equal 12. The $C_{22}$-cycloaliphatic tricarboxylic acids are made as Diels-Alder adducts of fatty acids, especially tall oil fatty acids and soya fatty acids, containing both non-conjugated and conjugated linoleic acids and fumaric acid reacted at from 170° C. to 270° C. in the presence of from 0.01% to 0.50% by weight of iodine. There is also disclosed herein the use of these $C_{22}$-cycloaliphatic tricarboxylic soaps as hydrotroping agents for normally insoluble nonionic synthetic detergents in alkaline mediums.

5 Claims, No Drawings

$C_{22}$-CYCLOALIPHATIC TRICARBOXYLIC FATTY ACID SOAPS

CROSS-REFERENCE TO RELATED APPLICATION

This application is a continuation-in-part of copending application Ser. No. 622,254 filed Oct. 14, 1975 now abandoned.

BACKGROUND OF THE INVENTION (1) Field of the Invention

This invention relates to soaps of $C_{22}$-cycloaliphatic tricarboxylic fatty acids. This invention also relates to a method for making the $C_{22}$-cycloaliphatic tricarboxylic fatty acid and the soaps as well as their use as hydrotroping agents for normally insoluble nonionic synthetic detergents in alkaline mediums. More particularly, this invention relates to $C_{22}$-cycloaliphatic tricarboxylic acids formed by the reaction of conjugated linoleic acid and fumaric acid via a Diels-Alder addition and soaps made therefrom.

(2) The Prior Art

Reactions of linoleic acid and linoleic acid containing natural fatty acid mixtures with fumaric acid are well known. In instances where no iodine is present and the temperature is above about 240° C., this reaction is known as the "ene" reaction where the addition occurs at a double bond site in the fatty acid chain forming a branched tricarboxylic acid. The "ene" reaction does not form a cycloaliphatic tricarboxylic acid; and in the usual case, the reaction temperatures are higher than Diels-Alder reactions and the "ene" reaction does not proceed cleanly in the presence of iodine. Examples of "ene" adducts are shown in German Patent No. 973,398 to Stein et al. Another example in U.S. Pat. No. 3,890,259 to Montesissa et al.

As stated, the subject invention includes making tricarboxylic acids that are Diels-Alder adducts. $C_{21}$-tribasic acids made from conjugated linoleic acid and dienophiles, such as maleic acid or maleic anhydride and the like, are disclosed in British Patent No. 1,032,363 and U.S. Pat. No. 3,412,056 both to Crawford et al., wherein conjugated fatty acids are isomerized to a trans/trans form and subsequently reacted with a reactive dienophile to form the Diels-Alder adduct. The Diels-Alder reaction was applied to fatty acids containing both conjugated linoleic acid and non-conjugated linoleic acid wherein the non-conjugated portion of the linoleic acid was also converted to a $C_{21}$-dicarboxylic acid using acrylic acid as the dienophile in Ward, U.S. Pat. No. 3,753,968 and soaps therefrom were taught in Ward, U.S. Pat. No. 3,734,859.

It is, therefore, a general object of this invention to provide new $C_{22}$-cycloaliphatic tricarboxylic acid soaps.

Another object of this invention is to provide a process for making $C_{22}$-cycloaliphatic tricarboxylic acids from all of the available linoleic acid in a fatty acid mixture.

Still another object of this invention is to provide a process whereby tall oil fatty acids and soya bean fatty acids may be converted into a $C_{22}$-cycloaliphatic tricarboxylic acid and an oleic acid portion and thereafter easily separated.

Yet another object of this invention is to provide a $C_{22}$-cycloaliphatic tricarboxylic acid as a hydrotroping agent for nonionic synthetic detergents.

Other objects, features and advantages will be evident from the following detailed description of the invention.

SUMMARY OF THE INVENTION

It has been found that if a fatty acid mixture containing a significant portion of non-conjugated and conjugated linoleic acid is treated with up to an equivalent weight percent of fumaric acid and from 0.01% to 0.50% by weight of said fatty acids of iodine at a temperature between 170° C. and 270° C., all of the linoleic acid portion of the fatty acid mixture is converted to a $C_{22}$-cycloaliphatic tricarboxylic acid. Thus, when the fatty acid mixture is a tall oil fatty acid or soya fatty acid mixture reacted with fumaric acid and the iodine and is heated, the $C_{22}$-cycloaliphatic tricarboxylic acid is formed with the remaining portion being mono-unsaturated and saturated fatty acids. Upon distillation, a high grade oleic-type acid is obtained and the residual being the $C_{22}$-cycloaliphatic tricarboxylic acid. The soaps are made from the $C_{22}$-cycloaliphatic tricarboxylic acid by neutralizing with any number of well known cations. Both the full soaps and mono-soaps may be made. These soaps may be utilized as hydrotroping agents.

DETAILED DESCRIPTION OF THE INVENTION (1) Process for Making the $C_{22}$-Tricarboxylic Acid There is provided by this invention a process for forming a $C_{22}$-cycloaliphatic tricarboxylic acid. Accordingly, fatty acid mixtures containing both non-conjugated linoleic acid and conjugated linoleic acid are reacted with fumaric acid in the presence of small amounts of iodine. The preferred fatty acids are the naturally occurring fatty acids high in linoleic acid content, e.g., above 50%, such as distilled tall oil fatty acid and soya fatty acid, corn oil fatty acid, cottonseed fatty acid, safflower fatty acid, sunflower fatty acid and the like. The process of this invention has an advantage over that described in U.S. Pat. No. 3,753,968 to Ward in that the use of the fumaric acid, unlike the acrylic acid, does not undergo thermal polymerization during the reaction at the conditions prescribed.

The fumaric acid is added to the fatty acid mixture in a stoichiometric amount. To this one-step process, catalytic amounts of iodine are used in amounts from 0.01% to 0.50% based on the weight of fatty acids, preferably 0.05% to 0.30% by weight. The amount of catalyst required varies inversely with the temperature. In order to maintain the highest possible yield of $C_{22}$-cycloaliphatic tricarboxylic acid from the fatty acid mixture, conditions close to the lower catalyst level and lower temperature are employed. Selection of the ideal amount of catalyst will depend upon the equipment, temperature and time of the reaction. The Diels-Alder addition is carried out at a temperature between 170° C. and 270° C., preferably 200° C. to 230° C. The reaction time at these preferred temperatures and under the preferred catalyst level is about 1 to 2 hours.

The following is typical of the general procedure which may be used to carry out the process of this invention on fatty acid mixtures containing both non-conjugated and conjugated linoleic acid.

To a fatty acid mixture is added a stoichiometric amount by weight of linoleic acids of fumaric acid and approximately 0.3% by weight of fatty acids of iodine at a temperature of about 200° C. The fumaric acid catalyzed by iodine readily undergoes a reaction with fatty acids. Therefore, when fatty acids, fumaric acid and iodine are mixed together and heated to the desired temperature, the non-conjugated portion of the linoleic acid material because of the presence of iodine is transformed to its conjugated form and then isomerized to the trans/trans form to enable it to partake in the Diels-Alder addition reaction; and all of the linoleic acid in the fatty acid mixture is converted to the $C_{22}$-cycloaliphatic tricarboxylic acid. In addition to the advantage of having a one-step reaction, it appears that the iodine catalyzes the addition reaction to a very clean, rapid reaction. This one-step process greatly improves the overall yield of $C_{22}$-cycloaliphatic tricarboxylic acid from fatty acids containing both non-conjugated and conjugated linoleic acids, because all of the linoleic acid is quickly converted to the tricarboxylic acid. The amount of tricarboxylic acid formed is approximately the same as the starting content of linoleic acid in the fatty acid mixture.

Whereas the linoleic acid portion of the fatty acids in the mixture is converted to the $C_{22}$-cycloaliphatic tricarboxylic acid, the remaining portion of the unsaturated materials is converted to an oleic-type fatty acid. In some applications, this mixture of tricarboxylic acid and oleic-type acid may be used. However, in other cases, it is desirable to use an essentially pure tricarboxylic acid. Whereas in the past it has been difficult to separate oleic acids from linoleic acids in normal distillation, the conversion of the linoleic acid portion of the fatty acid mixture to the $C_{22}$-cycloaliphatic tricarboxylic acid results in a mixture of fatty acids which are easily separated upon distillation to a high grade oleic acid and the $C_{22}$-cycloaliphatic tricarboxylic acid.

The $C_{22}$-cycloaliphatic tricarboxylic acids made from fumaric acid, unlike $C_{21}$-cycloaliphatic dicarboxylic acids, do not undergo thermal polymerization when excess dienophile is present; and, therefore, a product free of contamination by polymerized dienophile can be prepared. Also, because of the large difference in volatility between the tricarboxylic acid and the unreacted fatty acids, an essentially (<3%) mono-fatty acid free product can be prepared.

The $C_{22}$-cycloaliphatic tricarboxylic acid has the following structure;

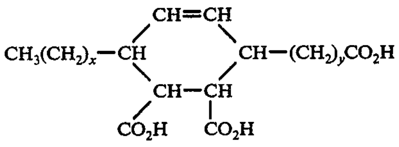

wherein $x$ and $y$ are integers from 3 to 9, and $x$ and $y$ together equal 12.

Typical commercially acceptable physical properties of the $C_{22}$-tricarboxylic acid (approximately 96% pure) are:

| | |
|---|---|
| Acid No. | >270 |
| Saponification No. | >285 |
| Color, Gardner | 7 |

(2) Soaps of the $C_{22}$-Cycloaliphatic Tricarboxylic Acid

The $C_{22}$-tricarboxylic acids are made into soaps with neutralizing agents which include those of the following cations, sodium, potassium, lithium and ammonium. These cations may be obtained from such inorganic alkalies as caustic soda, caustic potash and soda ash. Another cation which may be used is the ammonium cation. Organic amines may also be used, specifically amines such as triethylamine, monoethylamine, diethylamine and alkanolamines, such as ethanolamine, triethanolamine and diethanolamine.

The trisoaps of the $C_{22}$-cycloaliphatic tricarboxylic acid have the following structure;

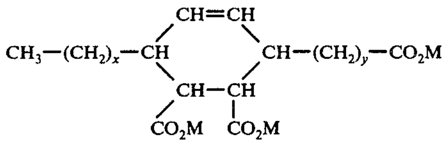

wherein $x$ and $y$ are integers from 3 to 9, $x$ and $y$ together equal 12, and M is a member of the group consisting of sodium, potassium, lithium, ammonium or organic amine described above. The trisoaps, or full soaps as they are also called, are made by simply mixing a stoichiometric amount of the cation desired.

In addition to the full soaps, the mono-soaps may be made by neutralizing with only enough of the cation, e.g., one-third the amount used for making the full soap, to react with the primary carboxyl. The mono-soaps thus are of the formula

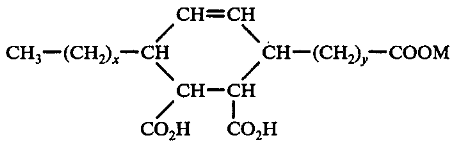

wherein $x$ and $y$ are integers from 3 to 9, $x$ and $y$ together equal 12, and M is a cation as described herein.

(3) $C_{22}$-Cycloaliphatic Tricarboxylic Acid Soaps as Hydrotroping Agents

Although both the trisoap and mono-soap of $C_{22}$-cycloaliphatic tricarboxylic acid have utility strictly as soaps, it has been found that the trisoaps of $C_{22}$-cycloaliphatic tricarboxylic acid also effectively function as hydrotropes for solubilizing ordinarily insoluble nonionic surfactants in highly alkaline systems. The trisodium salt of the $C_{22}$-cycloaliphatic tricarboxylic acid effectively solubilizes nonionic synthetic detergents in alkaline solutions containing more than 35% potassium hydroxide. Thus, clear composition at a pH of at least 7 containing a trisoap of $C_{22}$-cycloaliphatic tricarboxylic acid and nonionic surfactant in a weight ratio of 20:1 to 1:20, respectively, are provided. The preferred ratio of tricarboxylic acid salt to nonionic surfactant is 3:1 to 1:8. The effectiveness of a surfactant effective in both sodium and potassium-based alkaline systems is quite readily apparent to those skilled in the art.

Because the nonionic surfactants are insoluble in a high percentage at highly alkaline systems points out the desirability of being able to formulate an industrial cleaner at high alkalinity and high solids so that it can be shipped and stored as a concentrate and then diluted just prior to use. Various types of nonionic surfactants are well known to those skilled in the art and include, for example, polyoxyalkylene derivatives of polypropylene glycols sold under the trade name Pluronics, alkylphenoxy poly(oxyethylene)ethanols sold under the trade name Igepals, certain aliphatic polyethers sold under the trade name Antarox, and alcohol ethoxylates sold under the trade name Neodol.

The practice of this invention may clearly be seen in the following examples:

EXAMPLE 1

To illustrate the parameters desirable for the production of the $C_{22}$-cycloaliphatic tricarboxylic acid, a series of reactions involving the addition of fumaric acid to a tall oil fatty acid in an autoclave at various iodine levels and temperature/time conditions were run. The reaction conditions and results are shown in Table I.

In these reactions, at least 90% of the theoretical amount of fumaric acid required was allowed to react with tall oil fatty acid containing linoleic acid in the presence of iodine at several temperatures until all of the fumaric acid had been consumed. The effects of temperature and iodine level are illustrated by reactions A - E in Table I. As can be seen, the reaction occurs at 170° C.; but for maximum yield within a reasonable time, a temperature of about 200° C. is preferred.

From a theoretical acid number of 334, the actual acid number was 310, the saponification number 318 and the Gardner color 6.

EXAMPLE 3

This example illustrates the purification and characterization of the $C_{22}$-cycloaliphatic tricarboxylic acid. The fatty acid mixture Reaction Number F of Example 1 was distilled in a wiped film evaporator. The fatty acid mixture was fed at 16.5 pounds per hour. Heat for the distillation was supplied by a Dowtherm heater with heat in at 204° C. and out at 201° C. at a pressure of 0.06 torr. The results from the GLC are shown in Table II.

TABLE II

ANALYSIS OF DISTILLATION

| | | % by Weight |
|---|---|---|
| Distillate Fraction: | | 51.3 |
| fatty acids | 99.0 | |
| tricarboxylic acid | 1.0 | |
| Residue: | | 48.7 |
| fatty acid | 8.5 | |
| tricarboxylic acid | 91.5 | |
| | | 100.0 |

TABLE I

VARIATIONS IN REACTION CONDITIONS FOR REACTIONS OF DISTILLED TALL OIL FATTY ACIDS WITH FUMARIC ACID

| | Unreacted Tall Oil Fatty Acid | Reaction Number | | | | | | |
|---|---|---|---|---|---|---|---|---|
| | | A | B | C | D | E | F | G |
| A. Conditions | | | | | | | | |
| Temperature, ° C. | | 250 | 232 | 218 | 200 | 170 | 204 | 204 |
| Iodine, % | | 0.10 | 0.15 | 0.23 | 0.30 | 0.40 | 0.23 | 0.23 |
| Time, min. | | 45 | | | 145 | 240 | 115 | 165 |
| B. Analysis by GLC Assignment: | | | | | | | | |
| Saturated Fatty Acid | 5.1 | | 5.1 | 4.9 | 5.1 | 5.1 | 5.1 | |
| $C_{18}$-Monounsaturated Fatty Acid (oleic acid) | 45.0 | | 50.4 | 53.6 | 54.5 | 53.7 | 52.8 | |
| Linoleic Acid | 41.4 | | 8.8 | 2.9 | 2.6 | 6.7 | 2.3 | |
| Other Fatty Acids | 8.5 | | 1.1 | 3.6 | 2.4 | 2.0 | 5.2 | |
| $C_{22}$-Tricarboxylic Acid | 0.0 | | 34.6 | 35.0 | 35.4 | 33.0 | 34.6 | |
| C. Physical Properties: | | | | | | | | |
| Acid Number | 196 | 274 | 275 | 279 | 284 | 290 | 278 | 279 |
| Saponification Number | 197 | 295 | 293 | 293 | 295 | 293 | 287 | 289 |
| Color, Gardner | 3 | 7+ | 7 | 5+ | 5+ | 7+ | 7 | 11 |

The data in Table I clearly show that the saponification number remains constant, within experimental error, while the acid number decreases significantly with increasing reaction temperature. Even though a higher level of catalyst is required, the data in Table I also show that a lighter color reaction product results when the reaction is carried out at lower temperatures. Indications are that the titer of the fatty acid by-product is also reduced by reduction of reaction temperature. The data also show that prolonged heating, reactions E and G, is not detrimental to the chemical quality of the product.

EXAMPLE 2

This example illustrates making the fumaric adduct of soya fatty acids. A soya fatty acid containing about 85.6% unsaturated fatty acid of which 50.2% of the total fatty acids was non-conjugated and conjugated linoleic acid. To 600 grams of the soya fatty acids were added 1.5 grams (0.25%) of iodine and 130.5 grams of fumaric acid (52.9%). This mixture was reacted in an autoclave at 204° C. for 155 minutes. The final pressure was 80 p.s.i. GLC analysis showed that substantially all of the linoleic acid reaction gave tricarboxylic acid adduct that comprised 51% of the total final products.

For this distilled sample, the residue had an acid number of 358, a saponification number of 390, and a Gardner color of 8. Further, these results indicate it is doubtful if any "ene" reaction took place.

EXAMPLE 4

Soaps of the $C_{22}$-cycloaliphatic tricarboxylic acid are effective as a hydrotrope for solubilizing ordinarily insoluble nonionic synthetic detergents in alkaline systems. The maximum concentrations of various alkalies in which a 1:1 by weight (based on free acid) mixture of the trisoaps of potassium and sodium of the $C_{22}$-cycloaliphatic tricarboxylic acid and several nonionics are shown in Table III.

TABLE III

ALKALINE SOLUBILITY OF 1:1 TRICARBOXYLIC ACID TRISOAPS - NONIONIC MIXTURES

| Nonionic | Maximum Conc. of Tricarboxylic Acid/ Nonionic in KOH (%) until Cloudy | Maximum Conc. of Tricarboxylic Acid/ Nonionic in NaOH (%) until Cloudy |
|---|---|---|
| Pluronic®[1] L-61 | 39 | 11 |
| Pluronic®[1] L-62 | 35 | 24 |

TABLE III-continued

ALKALINE SOLUBILITY OF 1:1 TRICARBOXYLIC ACID TRISOAPS - NONIONIC MIXTURES

| Nonionic | Maximum Conc. of Tricarboxylic Acid/ Nonionic in KOH (%) until Cloudy | Maximum Conc. of Tricarboxylic Acid/ Nonionic in NaOH (%) until Cloudy |
|---|---|---|
| Igepal ®[2] CO-630 | 29 | 11 |

Notes:
[1]A registered trademark of Wyandotte Chemicals Corp. This nonionic is a polyoxyalkylene derivative of polypropylene glycol.
[2]A registered trademark of G.A.F. Corporation. This nonionic is an ethoxylated nonyl phenol.

These results show that the trisoaps of $C_{22}$-cycloaliphatic tricarboxylic acid are effective in solubilizing nonionic in alkalies. It has also been noted that a 1:8 ratio of the $C_{22}$-cycloaliphatic tricarboxylic acid soap to nonionic is sufficient to solubilize the nonionic in 20% potassium hydroxide solutions.

EXAMPLE 5

The trisodium soap of the tricarboxylic acid is a good wetting agent in alkaline systems and allows a reduction in the concentration of nonionic required to obtain a desired wetting speed. Igepal CO-630 is not effective by itself as a wetting agent in alkaline systems; but when mixed with the trisodium soap of the $C_{22}$-cycloaliphatic tricarboxylic acid, good wetting speeds were obtained as shown in Table IV wherein the trisodium soap of $C_{22}$-cycloaliphatic tricarboxylic acid was added (in parts per hundred, p.p.h.) to a 0.1% solution of Igepal CO-630 of 4% concentration of NaOH at 50° C.

TABLE IV

EFFECT OF TRISODIUM SOAP OF TRICARBOXYLIC ACID ON WETTING TIME

| Soap/ Igepal CO-630 (p.p.h.) | Draves Wetting Speed (Sec.) |
|---|---|
| 0 | Did not wet |
| 60 | 30 |
| 80 | 12 |
| 100 | 10 |
| 120 | 9 |
| 140 | 8 |
| 160 | 7 |

EXAMPLE 6

The effectiveness of other $C_{22}$-cycloaliphatic tricarboxylic acid soaps as cleaners are shown. These include the mono-potassium soap of $C_{22}$-cycloaliphatic tricarboxylic acid and the full potassium soap of the "kettle oil" from Run D of Example 1. The kettle oil is the mixture of $C_{22}$-cycloaliphatic tricarboxylic acid and oleic acid before distillation, such as shown in Example 3. The soaps were compared to linear alkyl benzene sulfonate (LAS), which is a commercially used hydrotrope.

TABLE V

| Hydrotrope | % | Neodol 25-7, % | Butyl Cellosolve | Number Strokes Necessery to Clean: Pencil | Grease Pencil |
|---|---|---|---|---|---|
| Full $K_3$ Soap | 0.5 | 0.4 | 2 | 21 | 40 |
| ⅓ K Soap | 0.5 | 0.4 | 2 | >50 | 50 |
| $K_3$ Soap Kettle Oil | 0.5 | 0.4 | 2 | 15 | 18 |

TABLE V-continued

| Hydrotrope | % | Neodol 25-7, % | Butyl Cellosolve | Number Strokes Necessery to Clean: Pencil | Grease Pencil |
|---|---|---|---|---|---|
| LAS | 0.5 | 0.4 | 2 | >50 | >50 |

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. A cycloaliphatic tricarboxylic fatty acid soap of the formula

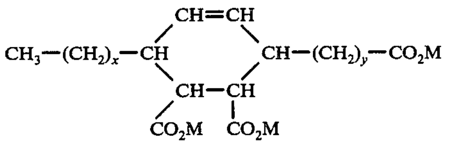

wherein $x$ and $y$ are integers from 3 to 9, $x$ and $y$ together equal 12, M is selected from the group consisting of sodium, potassium, lithium and ammonium.

2. The cycloaliphatic tricarboxylic acid soap according to claim 1 wherein M is sodium.

3. A cycloaliphatic tricarboxylic fatty acid soap of the formula

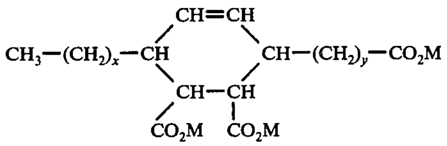

wherein $x$ and $y$ are integers from 3 to 9, $x$ and $y$ together equal 12, M is selected from the group consisting of triethylamine, diethylamine, monoethylamine, diethanolamine and ethanolamine.

4. A mono-soap of a cycloaliphatic tricarboxylic fatty acid of the formula

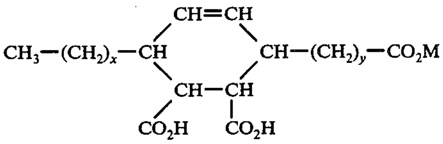

wherein $x$ and $y$ are integers from 3 to 9, $x$ and $y$ together equal 12, and M is a member of the group consisting of sodium, potassium, lithium and ammonium.

5. A mono-soap of a cycloaliphatic tricarboxylic fatty acid of the formula

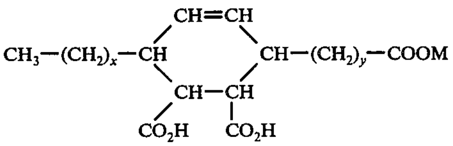

wherein $x$ and $y$ are integers from 3 to 9, $x$ and $y$ together equal 12, and M is a member of the group consisting of triethylamine, diethylamine, monoethylamine, diethanolamine and ethanolamine.

* * * * *